(12) United States Patent
Lee

(10) Patent No.: US 7,081,127 B1
(45) Date of Patent: Jul. 25, 2006

(54) FAR INFRARED PHYSIATRIC UNIT

(75) Inventor: Chyi-Ran Lee, Taipei (TW)

(73) Assignee: Far IR Medical Technology Co., Ltd., Taipei (TW)

( * ) Notice: Subject to any disclaimer, the term of this patent is extended or adjusted under 35 U.S.C. 154(b) by 30 days.

(21) Appl. No.: 11/047,682

(22) Filed: Feb. 2, 2005

(51) Int. Cl.
*A61N 5/00* (2006.01)

(52) U.S. Cl. .......................... 607/88; 607/100
(58) Field of Classification Search ............ 607/88–91, 607/100
See application file for complete search history.

(56) References Cited

U.S. PATENT DOCUMENTS

| | | | | |
|---|---|---|---|---|
| 2,474,472 A * | 6/1949 | Doyle | ...................... | 392/348 |
| 3,420,485 A * | 1/1969 | Price | ...................... | 248/188.3 |
| 5,621,846 A * | 4/1997 | Smith et al. | ............... | 392/376 |
| 6,317,636 B1 * | 11/2001 | Fujii | ...................... | 607/100 |
| 6,327,506 B1 * | 12/2001 | Yogo et al. | ............... | 607/100 |
| 6,549,809 B1 * | 4/2003 | Ono | ...................... | 607/100 |
| 6,709,384 B1 * | 3/2004 | Donnelly et al. | ........... | 600/22 |
| 2003/0074730 A1 * | 4/2003 | Ferber et al. | ............ | 4/622 |
| 2003/0103767 A1 * | 6/2003 | Kakuya et al. | ........... | 392/423 |
| 2003/0220593 A1 * | 11/2003 | Morton | ................ | 601/15 |
| 2005/0256554 A1 * | 11/2005 | Malak | .................. | 607/88 |

* cited by examiner

*Primary Examiner*—Henry M. Johnson, III
(74) *Attorney, Agent, or Firm*—Rabin & Berdo, P.C.

(57) ABSTRACT

A far infrared physiatric unit has a frame, an emitter and two adjustment knobs. The frame has two side boards and a supporting unit. The supporting unit is mounted between the side boards. The emitter is pivotally mounted between the side boards in the frame. A patient places his/her arm or foot on the supporting unit, and the emitter is adjusted to any position and angle to correspond to any position on the patient. The patient can be in a comfortable position during the far infrared treatment.

2 Claims, 6 Drawing Sheets

FAR INFRARED PHYSIATRIC UNIT

BACKGROUND OF THE INVENTION

1. Field of the Invention

The present invention relates to a far infrared physiatric unit, and more particularly to an emitter of the far infrared physiatric unit that attached to change its position and angle to emit the far infrared to any position of a patient's body.

2. Description of Related Art

Recently, people have learned that exposure to far infrared stimulates cell activity that promotes healing and improves health.

With reference to FIG. 6, the far infrared physiatric unit comprises a base (not shown), a flexible arm (40) and an emitter (41). The flexible arm (40) is mounted on the base. The emitter (41) is pivotally attached to a free end of the flexible arm (40).

When a patient is having far infrared treatment, a medical technician can adjust the height of the emitter (41) longitudinally to correspond to a position on a patient's the patient can receive the full benefit of the far infrared treatment.

However, the far infrared physiatric unit can only irradiate the patient's back, face, chest and arm with far infrared. If the patient's feet need to be irradiated with the far infrared, the patient has to lie down on a bed and curve the legs to a certain angle. For most patients, the far infrared irradiating the patients' feet is not very comfortable.

To overcome the shortcomings, the present invention provides a far infrared physiatric unit to obviate or mitigate the aforementioned problems.

SUMMARY OF THE INVENTION

The primary objective of the present invention is to provide a far infrared physiatric unit that can irradiate a patient with the patient in any comfort position.

The far infrared physiatric unit has a frame, an emitter and two supporting knobs. The frame has two side boards and a supporting unit. The supporting unit is mounted between the side boards. The emitter is pivotally mounted between the side boards in the frame. A patient places his/her arm or foot on the supporting unit, and the emitter is adjusted to any position and angle to correspond to any position on the patient. The patient can be in a comfortable position during the far infrared treatment.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
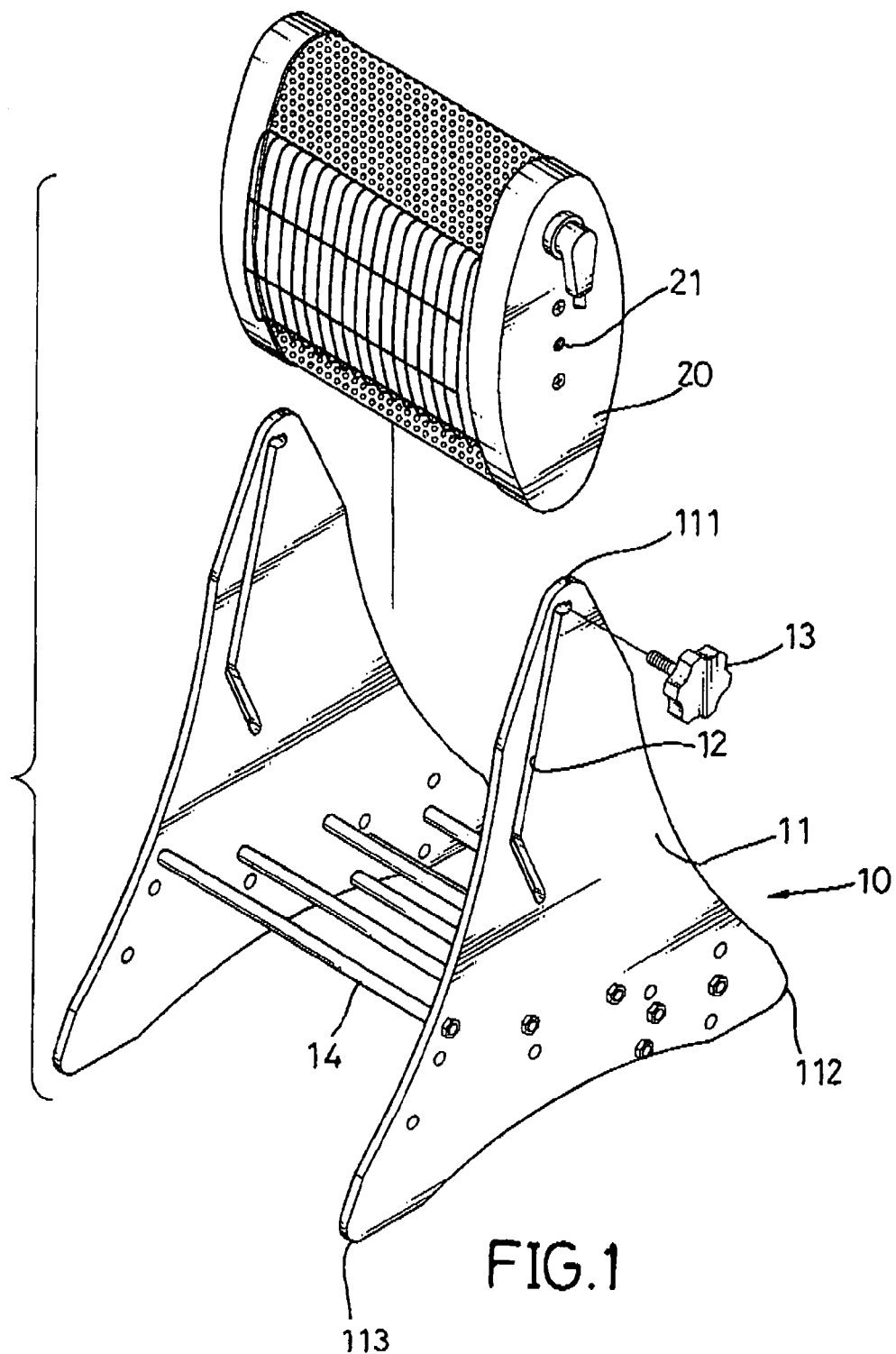
FIG. 1 is a partially exploded perspective view of a far infrared physiatric unit in accordance with the present invention.
Figure 2:
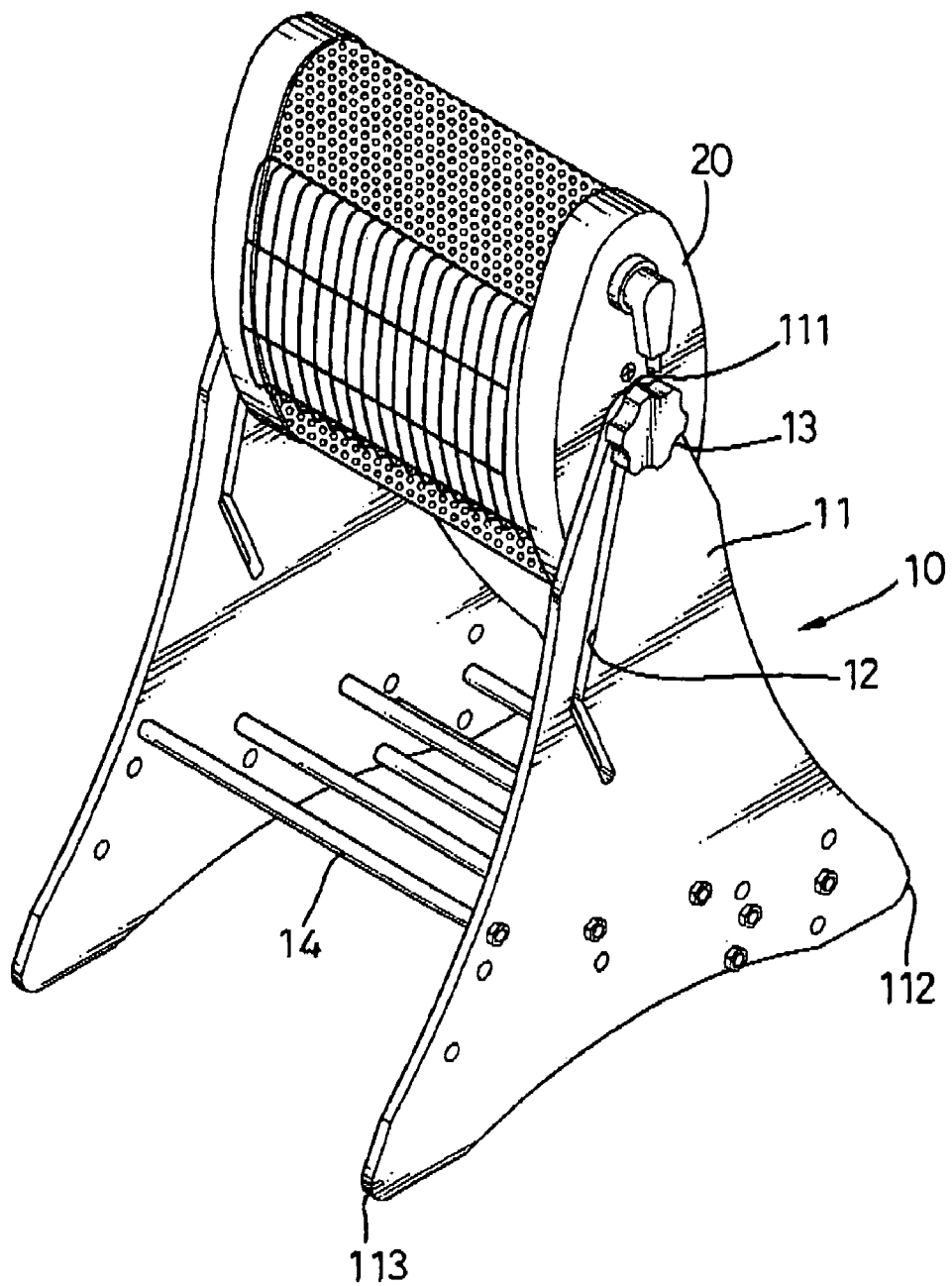
FIG. 2 is a perspective view of the far infrared physiatric unit in FIG. 1.

With reference to FIGS. 1 and 2, a far infrared physiatric unit in accordance with the present invention comprises a frame (10), an emitter (20) and two adjustment knobs (13).

The frame (10) has two side boards (11) and a supporting unit (14). Each side board (11) has a top end (111), a front bottom end (113), a rear bottom end (112) and a long hole (12). The long hole (12) is formed between the top end (111) and the front bottom end (113) of the side board (11). The supporting unit (14) is multiple rods separately mounted between the side boards (11) from the front bottom end (113) toward the rear bottom end (112).

The emitter (20) is pivotally mounted between side boards (11) and has two side ends. Each side end has a threaded hole (21) formed on the side end.

The adjustment knobs (13) extend respectively through long holes (12) of the side board (11) and screw respectively into the threaded hole (21) in the emitter (20) to hold the emitter (20) between the side boards (11).

Figure 3:
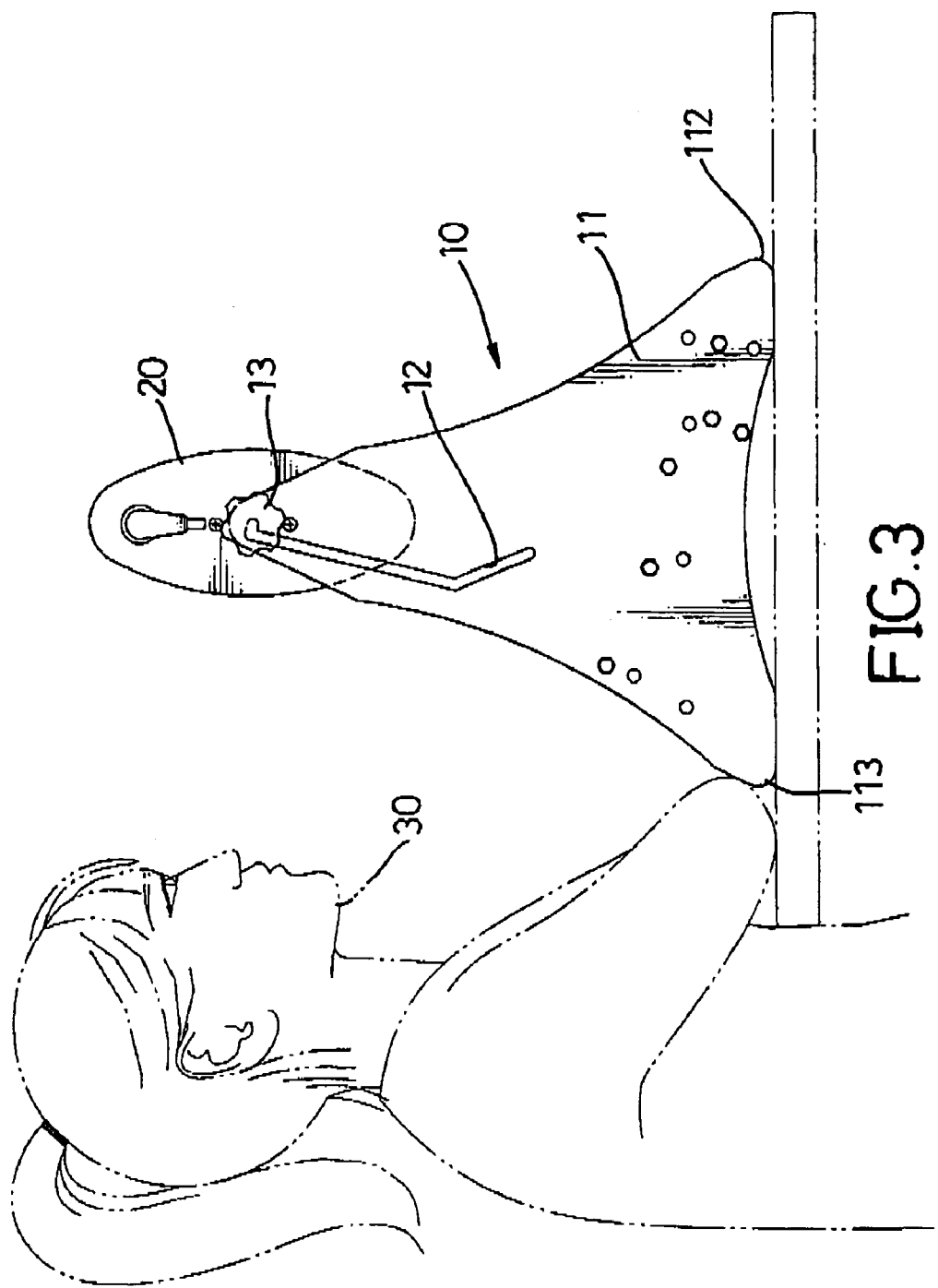
FIG. 3 is a side view of the far infrared physiatric unit in FIG. 1 with a patient's face facing the far infrared physiatric unit far infrared emitter.

With reference to FIG. 3, when a patient's face (30) is receiving the emitted far infrared, the frame (10) is placed on a table. The front bottom end (113) and the rear bottom end (112) of the side boards (11) rest on the table. The emitter (20) faces toward the face (30) of the patient and emits the far infrared to the patient's face (30).

Figure 4:
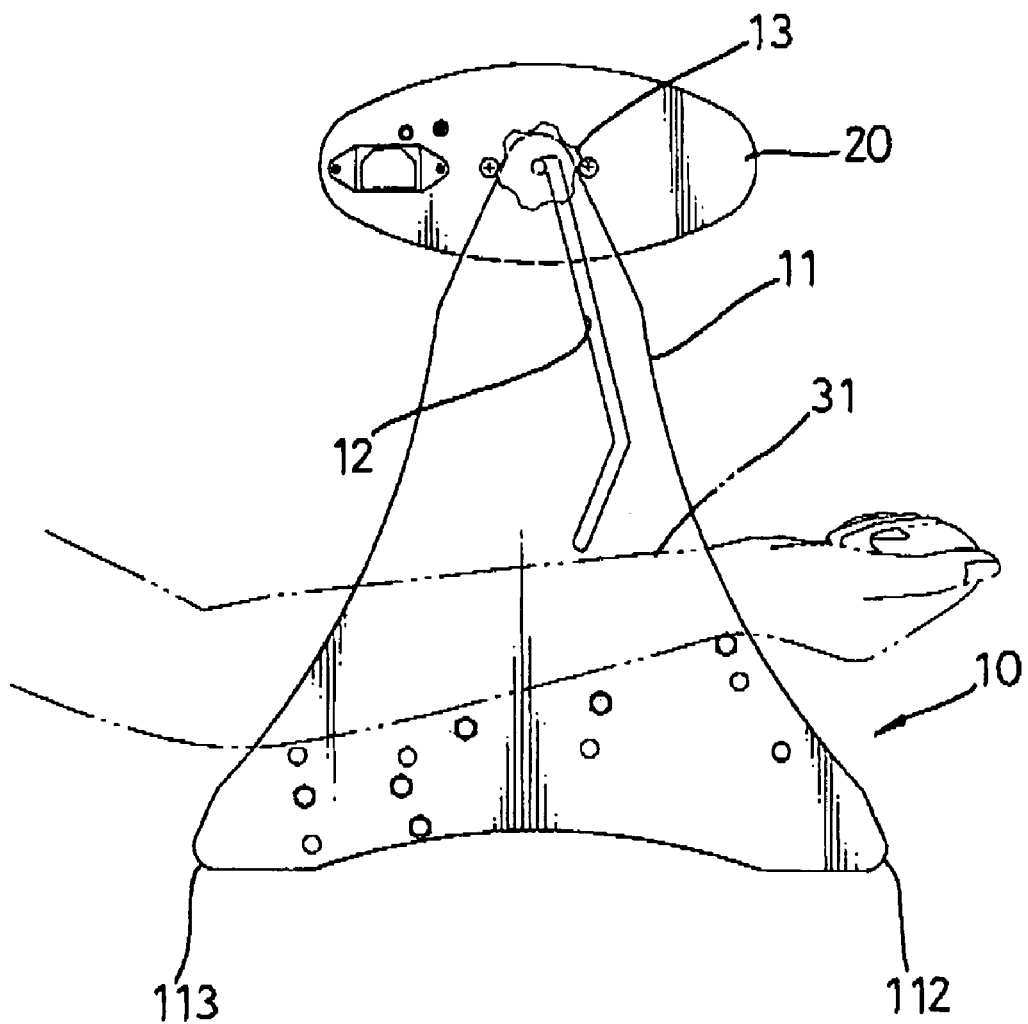
FIG. 4 is a side view of the far infrared physiatric unit in FIG. 1 with a patient's arm placed in the far infrared physiatric unit frame.

With reference to FIG. 4, for a patient's arm (31) is to receive the emitted far infrared, the arm (31) is placed on the supporting unit (14). The emitter (20) faces toward the arm (31) and emits the far infrared to the patient's arm (31). The emitter (20) can be moved in the log holes (12). When the emitter (20) is moved in the long holes (12), the distance between the emitter (20) and the arm (31) changes so that the patient can adjust-the distance between the arm (31) and the emitter (20).

Figure 5:
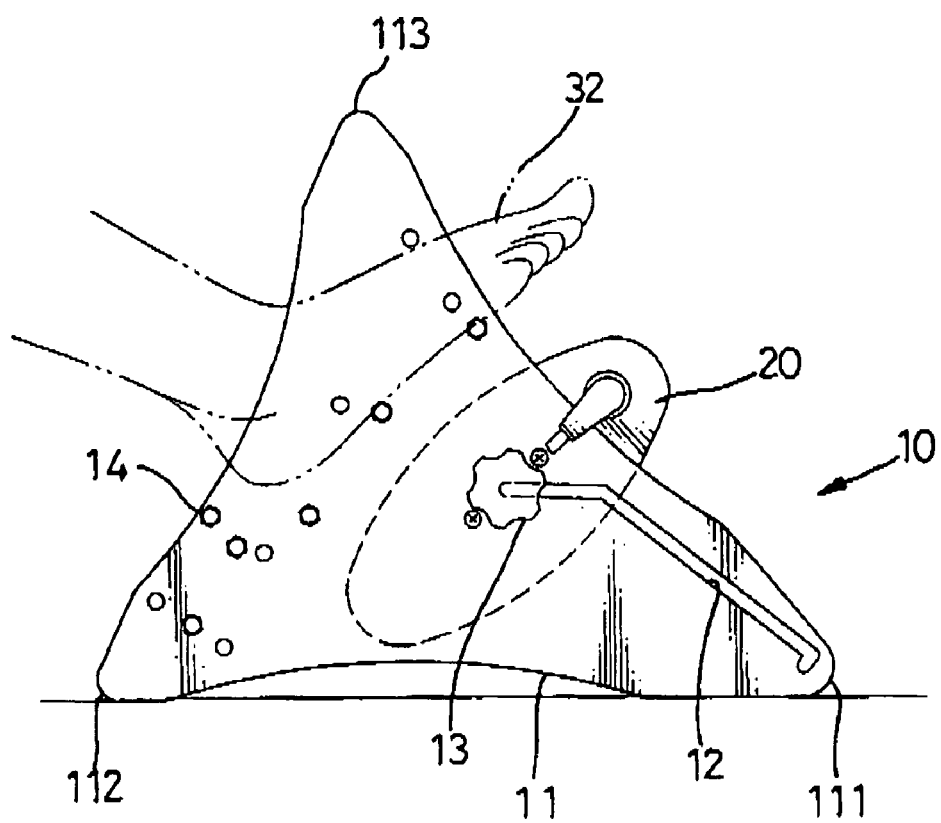
FIG. 5 is a side view of the far infrared physiatric unit in FIG. 1 with a patient's foot stepping on the far infrared physiatric unit supporting unit.
Figure 6:
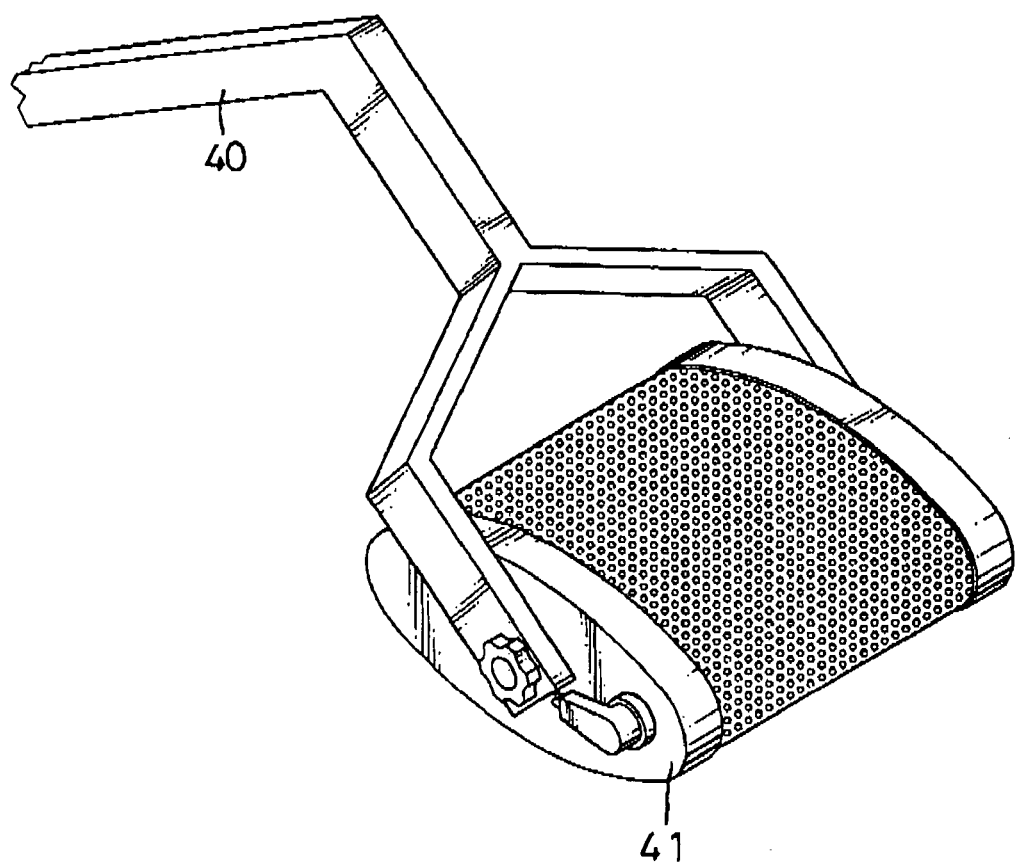
FIG. 6 is a partial perspective view of a conventional far infrared physiatric unit in accordance with the prior art.

With reference to FIG. 5, for a patient's foot (32) to receive the emitted far infrared, the frame (10) is placed on the floor. The top ends (111) and the rear bottom ends (112) touch the floor. The emitter (20) is moved toward the supporting unit (14). The foot (32) steps on the supporting frame (10). The emitter (20) faces the foot (32) and emits the far infrared to the feet (32).

In conclusion, the far infrared physiatric unit can be placed in any location, and the emitter (20) can be adjusted to any position by the long holes (13) to accommodate any part of the patient's body. The patient's body can be in a comfortable position when receiving the far infrared treatment.

Even though numerous characteristics and advantages of the present invention have been set forth in the foregoing description together with details of the structure and function of the invention, the disclosure is illustrative only. Changes may be made in detail especially in matters of shape, size, and arrangement of parts within the principles of the invention to the full extent indicated by the broad general meaning of the terms in which the appended claims are expressed.

What is claimed is:

1. A far infrared physiatric unit comprises
a frame having
two side boards, each side board having
a top end;
a front bottom end;
a rear bottom end;
a long hole formed through the board;
a supporting unit mounted between the side boards; an emitter pivotally mounted between the side boards and having two side ends, each side end having a threaded hole formed on the side end; and
two adjustment knobs extending respectively through the long holes in the side boards and screwing respectively into the threaded holes to hold the emitter between the side boards.

2. The far infrared physiatric unit as claimed in claim 1, wherein the supporting unit is multiple bars mounted between the side boards.

* * * * *